United States Patent
Belew

(10) Patent No.: US 8,890,511 B2
(45) Date of Patent: Nov. 18, 2014

(54) TARGETING OPERATION SITES

(75) Inventor: Kevin Wayne Belew, Hernando, MS (US)

(73) Assignee: Smith & Nephew, Inc., Memphis, TN (US)

(*) Notice: Subject to any disclaimer, the term of this patent is extended or adjusted under 35 U.S.C. 154(b) by 365 days.

(21) Appl. No.: 13/358,065

(22) Filed: Jan. 25, 2012

(65) Prior Publication Data

US 2012/0187941 A1 Jul. 26, 2012

Related U.S. Application Data

(60) Provisional application No. 61/436,047, filed on Jan. 25, 2011.

(51) Int. Cl.
| | |
|---|---|
| *G01B 7/14* | (2006.01) |
| *A61B 18/08* | (2006.01) |
| *A61B 18/14* | (2006.01) |
| *A61B 5/06* | (2006.01) |
| *A61B 5/00* | (2006.01) |
| *A61B 17/34* | (2006.01) |
| *A61B 19/00* | (2006.01) |

(52) U.S. Cl.
CPC ..... *A61B 17/3403* (2013.01); *A61B 2019/5251* (2013.01); *A61B 19/56* (2013.01); *A61B 2019/5272* (2013.01); *A61B 19/5244* (2013.01); *A61B 2019/507* (2013.01); *A61B 5/062* (2013.01); *A61B 5/4571* (2013.01); *A61B 5/4504* (2013.01)
USPC ............ 324/207.11; 324/207.13; 606/39; 606/45

(58) Field of Classification Search
USPC .................................................. 324/207.11
See application file for complete search history.

(56) References Cited

U.S. PATENT DOCUMENTS

| | | | |
|---|---|---|---|
| 3,219,969 | A | 11/1965 | Snavely |
| 4,353,110 | A | 10/1982 | Ellis |

(Continued)

FOREIGN PATENT DOCUMENTS

| | | |
|---|---|---|
| CA | 2571508 A1 | 1/2006 |
| CN | 2698283 Y | 5/2005 |

(Continued)

OTHER PUBLICATIONS

Ekliptik, Guiding Star, Lidis: The Best Solution for Distal Interlocking, 2008, 2 pages.

(Continued)

*Primary Examiner* — Bot Ledynh
(74) *Attorney, Agent, or Firm* — Fish & Richardson P.C.

(57) ABSTRACT

A system for targeting an operation site includes an identifier having an electromagnetic field generator configured to produce electromagnetic fields. The system includes an implement that includes a handle, a blade portion, and an electromagnetic field sensor coupled to the blade portion. The electromagnetic field sensor is configured to produce a signal responsive to electromagnetic fields produced by the electromagnetic field generator. The system includes a control unit configured to access information indicating a position of the electromagnetic field sensor relative to the operation site, receive a signal from the electromagnetic field sensor that is indicative of a position of a tool relative to the electromagnetic field sensor, and determine a position of the tool relative to an operation site based on the received signal and the position of the electromagnetic field sensor relative to the operation site.

17 Claims, 9 Drawing Sheets

(56) References Cited

U.S. PATENT DOCUMENTS

| | | |
|---|---|---|
| 4,532,599 A | 7/1985 | Smith |
| 4,621,628 A | 11/1986 | Brudermann |
| D297,047 S | 8/1988 | Hon et al. |
| 4,794,930 A | 1/1989 | Machida et al. |
| 5,049,151 A | 9/1991 | Durham et al. |
| 5,127,913 A | 7/1992 | Thomas |
| 5,217,009 A | 6/1993 | Kronberg |
| 5,251,127 A | 10/1993 | Raab |
| 5,281,224 A | 1/1994 | Faccioli et al. |
| 5,320,625 A | 6/1994 | Bertin |
| 5,361,766 A | 11/1994 | Nichols et al. |
| 5,383,917 A | 1/1995 | Desai et al. |
| 5,411,503 A | 5/1995 | Hollstien et al. |
| 5,417,688 A | 5/1995 | Elstrom et al. |
| 5,433,720 A | 7/1995 | Faccioli et al. |
| 5,514,145 A | 5/1996 | Durham et al. |
| 5,580,156 A | 12/1996 | Suzuki et al. |
| 5,584,838 A | 12/1996 | Rona et al. |
| 5,585,783 A | 12/1996 | Hall |
| 5,957,836 A | 9/1999 | Johnson |
| 5,957,934 A | 9/1999 | Rapoport |
| 6,009,878 A | 1/2000 | Weijand et al. |
| 6,036,696 A | 3/2000 | Lambrecht et al. |
| 6,039,742 A | 3/2000 | Krettek et al. |
| 6,074,394 A | 6/2000 | Krause |
| 6,081,741 A | 6/2000 | Hollis |
| 6,106,528 A | 8/2000 | Durham |
| 6,157,853 A | 12/2000 | Blume et al. |
| 6,162,228 A | 12/2000 | Durham |
| 6,174,335 B1 | 1/2001 | Varieur et al. |
| 6,212,419 B1 | 4/2001 | Blume et al. |
| 6,233,490 B1 | 5/2001 | Kasevich |
| 6,267,770 B1 | 7/2001 | Truwit |
| 6,304,091 B1 | 10/2001 | Shahoian et al. |
| 6,311,082 B1 | 10/2001 | Creighton et al. |
| 6,474,341 B1 | 11/2002 | Hunter et al. |
| 6,503,249 B1 | 1/2003 | Krause |
| 6,575,973 B1 | 6/2003 | Shekalim |
| 6,636,757 B1 | 10/2003 | Jascob et al. |
| 6,675,491 B2 | 1/2004 | Sasaki et al. |
| 6,694,168 B2 | 2/2004 | Traxel et al. |
| 6,718,194 B2 | 4/2004 | Kienzle |
| 6,747,253 B1 | 6/2004 | Firth et al. |
| 6,807,446 B2 | 10/2004 | Fenn et al. |
| 6,890,332 B2 | 5/2005 | Truckai et al. |
| 6,991,655 B2 | 1/2006 | Iversen |
| 7,001,346 B2 | 2/2006 | White |
| 7,029,478 B2 | 4/2006 | Hollstien et al. |
| 7,060,075 B2 | 6/2006 | Govari et al. |
| D528,211 S | 9/2006 | Solar et al. |
| 7,130,676 B2 | 10/2006 | Barrick |
| 7,152,608 B2 | 12/2006 | Hunter et al. |
| 7,217,276 B2 | 5/2007 | Henderson et al. |
| 7,253,611 B2 | 8/2007 | Ma |
| 7,294,133 B2 | 11/2007 | Zink et al. |
| 7,295,184 B2 | 11/2007 | Suprun et al. |
| 7,358,481 B2 | 4/2008 | Yeoh et al. |
| 7,477,926 B2 | 1/2009 | McCombs |
| 7,532,997 B2 | 5/2009 | Li et al. |
| 7,542,791 B2 | 6/2009 | Mire et al. |
| 7,549,960 B2 | 6/2009 | Govari |
| 7,559,931 B2 | 7/2009 | Stone |
| 7,575,550 B1 | 8/2009 | Govari |
| 7,634,306 B2 | 12/2009 | Sarin et al. |
| 7,686,818 B2 | 3/2010 | Simon et al. |
| 7,702,379 B2 | 4/2010 | Avinash et al. |
| 7,727,240 B1 | 6/2010 | Benton |
| 7,729,742 B2 | 6/2010 | Govari |
| 7,780,681 B2 | 8/2010 | Sarin et al. |
| 7,785,330 B2 | 8/2010 | Sherman et al. |
| 7,835,785 B2 | 11/2010 | Scully et al. |
| 7,840,254 B2 | 11/2010 | Glossop |
| 7,846,162 B2 | 12/2010 | Nelson et al. |
| 7,918,853 B2 | 4/2011 | Watanabe et al. |
| 7,925,068 B2 | 4/2011 | Hoctor et al. |
| 7,927,338 B2 | 4/2011 | Laffargue et al. |
| 7,949,386 B2 | 5/2011 | Buly et al. |
| 7,955,280 B2 | 6/2011 | Radinsky et al. |
| 8,007,448 B2 | 8/2011 | Moctezuma de La Barrera |
| 8,057,479 B2 | 11/2011 | Stone |
| 8,066,706 B2 | 11/2011 | Schlienger et al. |
| 8,167,823 B2 | 5/2012 | Nycz et al. |
| 8,176,922 B2 | 5/2012 | Sherman et al. |
| 8,197,494 B2 | 6/2012 | Jaggi et al. |
| 8,211,108 B2 | 7/2012 | Matityahu |
| 8,241,296 B2 | 8/2012 | Wasielewski |
| 8,301,262 B2 | 10/2012 | Mi et al. |
| 8,337,426 B2 | 12/2012 | Nycz |
| 8,400,312 B2 | 3/2013 | Hotokebuchi et al. |
| 8,623,023 B2 | 1/2014 | Ritchey |
| 2002/0032445 A1 | 3/2002 | Fujiwara |
| 2002/0052604 A1 | 5/2002 | Simon et al. |
| 2002/0077540 A1 | 6/2002 | Kienzle |
| 2002/0173792 A1 | 11/2002 | Severns et al. |
| 2003/0105470 A1 | 6/2003 | White |
| 2003/0120150 A1 | 6/2003 | Govari |
| 2003/0135211 A1 | 7/2003 | Cho |
| 2003/0153829 A1 | 8/2003 | Sarin et al. |
| 2003/0164172 A1 | 9/2003 | Chumas et al. |
| 2003/0208122 A1 | 11/2003 | Melkent et al. |
| 2004/0011365 A1 | 1/2004 | Govari et al. |
| 2004/0034355 A1 | 2/2004 | Govari et al. |
| 2004/0097952 A1 | 5/2004 | Sarin et al. |
| 2004/0147926 A1 | 7/2004 | Iversen |
| 2004/0230199 A1 | 11/2004 | Jansen et al. |
| 2004/0243148 A1 | 12/2004 | Wasielewski |
| 2004/0254584 A1 | 12/2004 | Sarin et al. |
| 2005/0027301 A1 | 2/2005 | Stihl |
| 2005/0027304 A1 | 2/2005 | Leloup et al. |
| 2005/0035115 A1 | 2/2005 | Anderson et al. |
| 2005/0035116 A1 | 2/2005 | Brown et al. |
| 2005/0043726 A1 | 2/2005 | McHale et al. |
| 2005/0059885 A1 | 3/2005 | Melkent et al. |
| 2005/0070916 A1 | 3/2005 | Hollstien et al. |
| 2005/0075562 A1 | 4/2005 | Szakelyhidi et al. |
| 2005/0075632 A1 | 4/2005 | Russell et al. |
| 2005/0080335 A1 | 4/2005 | Simon et al. |
| 2005/0080427 A1 | 4/2005 | Govari et al. |
| 2005/0085714 A1 | 4/2005 | Foley et al. |
| 2005/0085715 A1 | 4/2005 | Dukesherer et al. |
| 2005/0099290 A1 | 5/2005 | Govari |
| 2005/0124988 A1 | 6/2005 | Terrill-Grisoni et al. |
| 2005/0143726 A1 | 6/2005 | Bortkiewicz |
| 2005/0148855 A1 | 7/2005 | Kienzle |
| 2005/0149050 A1 | 7/2005 | Stifter et al. |
| 2005/0197569 A1 | 9/2005 | McCombs |
| 2005/0228270 A1 | 10/2005 | Lloyd et al. |
| 2005/0242087 A1 | 11/2005 | Anderson et al. |
| 2005/0245821 A1 | 11/2005 | Govari et al. |
| 2005/0261700 A1 | 11/2005 | Tuma et al. |
| 2006/0015031 A1 | 1/2006 | Kienzle |
| 2006/0029186 A1 | 2/2006 | De Villiers et al. |
| 2006/0052782 A1 | 3/2006 | Morgan et al. |
| 2006/0074405 A1 | 4/2006 | Malackowski et al. |
| 2006/0084867 A1 | 4/2006 | Tremblay et al. |
| 2006/0095047 A1 | 5/2006 | de la Barrera |
| 2006/0106400 A1 | 5/2006 | Fernandez et al. |
| 2006/0142656 A1 | 6/2006 | Malackowski et al. |
| 2006/0184177 A1 | 8/2006 | Echeverri |
| 2006/0190011 A1 | 8/2006 | Ries |
| 2006/0264731 A1 | 11/2006 | Murphy |
| 2006/0282168 A1 | 12/2006 | Sherman |
| 2006/0287613 A1 | 12/2006 | Amiot et al. |
| 2006/0293593 A1 | 12/2006 | Govari et al. |
| 2006/0293614 A1 | 12/2006 | Radinsky et al. |
| 2007/0093709 A1 | 4/2007 | Abernathie |
| 2007/0129629 A1 | 6/2007 | Beauregard et al. |
| 2007/0162018 A1 | 7/2007 | Jensen et al. |
| 2007/0167744 A1 | 7/2007 | Beauregard et al. |
| 2007/0191827 A1 | 8/2007 | Lischinsky et al. |
| 2007/0208251 A1 | 9/2007 | Anderson et al. |
| 2007/0225595 A1 | 9/2007 | Malackowski et al. |
| 2007/0249967 A1 | 10/2007 | Buly et al. |
| 2007/0255132 A1 | 11/2007 | Shalgi et al. |

(56) References Cited

U.S. PATENT DOCUMENTS

| | | |
|---|---|---|
| 2007/0276370 A1 | 11/2007 | Altarac et al. |
| 2007/0282440 A1 | 12/2007 | Visentin |
| 2008/0015551 A1 | 1/2008 | Feine |
| 2008/0021309 A1 | 1/2008 | Amiot et al. |
| 2008/0039857 A1 | 2/2008 | Giersch et al. |
| 2008/0051910 A1 | 2/2008 | Kammerzell et al. |
| 2008/0071142 A1 | 3/2008 | Gattani et al. |
| 2008/0086145 A1 | 4/2008 | Sherman et al. |
| 2008/0146969 A1 | 6/2008 | Kurtz |
| 2008/0154266 A1 | 6/2008 | Protopsaltis et al. |
| 2008/0221628 A1 | 9/2008 | Milbocker et al. |
| 2008/0228195 A1 | 9/2008 | von Jako et al. |
| 2008/0255560 A1 | 10/2008 | Myers et al. |
| 2008/0255584 A1 | 10/2008 | Beverland et al. |
| 2008/0269596 A1 | 10/2008 | Revie et al. |
| 2008/0281326 A1 | 11/2008 | Watanabe et al. |
| 2008/0281334 A1 | 11/2008 | Zheng et al. |
| 2009/0024023 A1 | 1/2009 | Welches et al. |
| 2009/0054910 A1 | 2/2009 | Zheng et al. |
| 2009/0088756 A1 | 4/2009 | Anderson |
| 2009/0099404 A1 | 4/2009 | Kraus et al. |
| 2009/0099665 A1 | 4/2009 | Taylor et al. |
| 2009/0125117 A1 | 5/2009 | Paradis et al. |
| 2009/0138019 A1 | 5/2009 | Wasielewski |
| 2009/0165573 A1 | 7/2009 | Ledoux et al. |
| 2009/0171370 A1 | 7/2009 | Yoon et al. |
| 2009/0177080 A1 | 7/2009 | Kristan et al. |
| 2009/0227862 A1 | 9/2009 | Smith et al. |
| 2009/0306665 A1 | 12/2009 | Lerner et al. |
| 2009/0306666 A1 | 12/2009 | Czartoski et al. |
| 2009/0326537 A1 | 12/2009 | Anderson |
| 2010/0041985 A1 | 2/2010 | Simon et al. |
| 2010/0063508 A1 | 3/2010 | Borja et al. |
| 2010/0064216 A1 | 3/2010 | Borja et al. |
| 2010/0069911 A1 | 3/2010 | Borja et al. |
| 2010/0076505 A1 | 3/2010 | Borja |
| 2010/0100011 A1 | 4/2010 | Roche |
| 2010/0137869 A1 | 6/2010 | Borja et al. |
| 2010/0137871 A1 | 6/2010 | Borja |
| 2010/0145337 A1 | 6/2010 | Janna et al. |
| 2010/0152566 A1 | 6/2010 | Rains et al. |
| 2010/0152573 A1 | 6/2010 | Ritchey et al. |
| 2010/0211177 A1 | 8/2010 | Abdou |
| 2010/0249657 A1 | 9/2010 | Nycz et al. |
| 2010/0249796 A1 | 9/2010 | Nycz |
| 2010/0256635 A1* | 10/2010 | Mckenna et al. ............... 606/45 |
| 2010/0261998 A1 | 10/2010 | Stiehl |
| 2010/0274121 A1 | 10/2010 | Ritchey et al. |
| 2010/0274253 A1 | 10/2010 | Ure |
| 2010/0274256 A1 | 10/2010 | Ritchey et al. |
| 2010/0274306 A1 | 10/2010 | Pastore et al. |
| 2010/0289491 A1 | 11/2010 | Budker et al. |
| 2010/0312245 A1 | 12/2010 | Tipirneni et al. |
| 2011/0060339 A1 | 3/2011 | de Wekker |
| 2011/0082366 A1 | 4/2011 | Scully et al. |
| 2011/0109311 A1 | 5/2011 | Walsh |
| 2011/0130765 A1 | 6/2011 | Fernandez |
| 2011/0208037 A1 | 8/2011 | Rains et al. |
| 2011/0257518 A1 | 10/2011 | Buly et al. |
| 2011/0270080 A1 | 11/2011 | Crane |
| 2011/0276053 A1 | 11/2011 | Birkbeck et al. |
| 2011/0288600 A1 | 11/2011 | Ritchey |
| 2011/0295108 A1 | 12/2011 | Cox et al. |
| 2011/0295253 A1 | 12/2011 | Bonutti et al. |
| 2012/0010500 A1 | 1/2012 | Couture et al. |
| 2012/0022406 A1 | 1/2012 | Hladio et al. |
| 2012/0035468 A1 | 2/2012 | Ritchey et al. |
| 2012/0091122 A1 | 4/2012 | Ahmad et al. |
| 2012/0101361 A1 | 4/2012 | Rains |
| 2012/0130279 A1 | 5/2012 | Stone |
| 2012/0136402 A1 | 5/2012 | Burroughs |
| 2012/0143047 A1 | 6/2012 | Kimura et al. |
| 2012/0157887 A1 | 6/2012 | Fanson et al. |
| 2012/0184844 A1 | 7/2012 | Gielen et al. |
| 2012/0209117 A1 | 8/2012 | Mozes et al. |
| 2012/0220107 A1 | 8/2012 | Fukuda et al. |
| 2012/0226094 A1 | 9/2012 | Ritchey |
| 2012/0227542 A1 | 9/2012 | Koch |
| 2012/0232561 A1 | 9/2012 | Fernandez |
| 2012/0245647 A1 | 9/2012 | Kunz et al. |
| 2012/0253354 A1 | 10/2012 | Arlettaz |
| 2012/0277752 A1 | 11/2012 | Wasielewski |
| 2012/0283599 A1 | 11/2012 | Borja |
| 2012/0323247 A1 | 12/2012 | Bettenga |
| 2012/0330319 A1 | 12/2012 | Birkbeck et al. |
| 2013/0046310 A1 | 2/2013 | Ranawat et al. |
| 2013/0053856 A1 | 2/2013 | Penenberg |
| 2013/0053858 A1 | 2/2013 | Penenberg |
| 2013/0053904 A1 | 2/2013 | Penenberg |
| 2013/0066323 A1 | 3/2013 | Nycz et al. |
| 2013/0131679 A1 | 5/2013 | Janna |
| 2013/0218007 A1 | 8/2013 | Petteys |
| 2013/0289573 A1 | 10/2013 | Heilala |

FOREIGN PATENT DOCUMENTS

| | | |
|---|---|---|
| CN | 201029876 Y | 3/2008 |
| DE | 102008023760 A1 | 12/2009 |
| EP | 523905 A3 | 5/1993 |
| EP | 628287 A3 | 4/1995 |
| EP | 1391181 A1 | 2/2004 |
| EP | 1570782 A2 | 9/2005 |
| EP | 1382308 A3 | 11/2005 |
| EP | 1570781 B1 | 9/2009 |
| EP | 2130511 A1 | 12/2009 |
| EP | 1563810 B1 | 3/2010 |
| EP | 1743590 B1 | 10/2010 |
| EP | 1803394 B1 | 1/2012 |
| EP | 2294980 B1 | 3/2012 |
| GR | 1005791 B2 | 1/2008 |
| WO | WO9421209 A1 | 9/1994 |
| WO | WO9500085 A1 | 1/1995 |
| WO | WO9713467 A1 | 4/1997 |
| WO | WO9832387 A1 | 7/1998 |
| WO | WO9947052 A1 | 9/1999 |
| WO | WO0134016 A3 | 10/2001 |
| WO | WO02062250 A1 | 8/2002 |
| WO | WO03044556 A2 | 5/2003 |
| WO | WO03073951 A1 | 9/2003 |
| WO | WO03041611 A3 | 12/2003 |
| WO | WO03105659 A2 | 12/2003 |
| WO | WO2004030556 A2 | 4/2004 |
| WO | WO2004001569 B1 | 7/2004 |
| WO | WO2004069063 A1 | 8/2004 |
| WO | WO2004069063 A3 | 8/2004 |
| WO | WO2004091419 A8 | 11/2004 |
| WO | WO2004112610 A2 | 12/2004 |
| WO | WO2005000140 A2 | 1/2005 |
| WO | WO2005009303 A1 | 2/2005 |
| WO | WO2005023110 A1 | 3/2005 |
| WO | WO2005051241 A1 | 6/2005 |
| WO | WO2005087125 A2 | 9/2005 |
| WO | WO2005120203 A2 | 12/2005 |
| WO | WO2006060632 A1 | 6/2006 |
| WO | WO2006067634 A1 | 6/2006 |
| WO | WO2006109983 A1 | 10/2006 |
| WO | WO2005084572 A3 | 11/2006 |
| WO | WO2006128301 A1 | 12/2006 |
| WO | WO2007025191 A1 | 3/2007 |
| WO | WO2007009088 A3 | 5/2007 |
| WO | WO2007061890 A2 | 5/2007 |
| WO | WO2006094119 A3 | 11/2007 |
| WO | WO2007133168 A2 | 11/2007 |
| WO | WO2008014618 A1 | 2/2008 |
| WO | WO2008105874 A1 | 9/2008 |
| WO | WO2008106593 A3 | 11/2008 |
| WO | WO2009046547 A1 | 4/2009 |
| WO | WO2009062314 A1 | 5/2009 |
| WO | WO2009108214 A1 | 9/2009 |
| WO | WO2009131999 A2 | 10/2009 |
| WO | WO2010011978 A1 | 1/2010 |
| WO | WO2010028046 A1 | 3/2010 |
| WO | WO2010030809 A1 | 3/2010 |
| WO | WO2010052500 A2 | 5/2010 |

(56) References Cited

FOREIGN PATENT DOCUMENTS

| WO | WO2010063117 A1 | 6/2010 |
|---|---|---|
| WO | WO2010099247 A2 | 9/2010 |
| WO | WO2010111272 A1 | 9/2010 |
| WO | WO2010129141 A2 | 11/2010 |
| WO | WO2010129308 A2 | 11/2010 |
| WO | WO2011060536 A1 | 5/2011 |
| WO | WO2011124661 A1 | 10/2011 |
| WO | WO2012080840 A1 | 6/2012 |
| WO | WO2012084739 A1 | 6/2012 |
| WO | WO2012100825 A1 | 8/2012 |
| WO | WO2013025927 A2 | 2/2013 |
| WO | WO2013049534 A1 | 4/2013 |

OTHER PUBLICATIONS

International Search Report for International Application No. PCT/US2008/055300, mailed Sep. 17, 2008, 3 pages.
International Preliminary Report on Patentability and Written Opinion for International Application No. PCT/US2008/055300, mailed Sep. 1, 2009, 6 pages.
International Preliminary Report on Patentability and Written Opinion for International Application No. PCT/US2007/063001, mailed Sep. 1, 2009, 5 pages.
International Search Report for International Application No. PCT/US2007/063001, mailed Nov. 30, 2007, 3 pages.
Office Action for European Application 08872996.7-1269, Jul. 21, 2011, 5 pages.
International Search Report for International Application No. PCT/US2008/074520, mailed Jan. 23, 2009, 2 pages.
Ekliptik, "Guiding Star", reprinted from http://ekliptik.si/content/view/37/42, on Jul. 1, 2010, 2 pages.
Ritchey, et al., U.S. Appl. No. 29/376,026, filed Sep. 30, 2010.
International Search Report and Written Opinion for International Application No. PCT/US2010/032634, mailed Jan. 26, 2011, 10 pages.
International Search Report and Written Opinion for PCT/US2010/030784, mailed Oct. 29, 2010, 11 pages.
European Search Report for European Application No. 07830964.7, mailed Jun. 18, 2010, 4 pages.
Office Action for Chinese Application No. 200880006490.9, mailed Mar. 31, 2011, 13 pages.
International Search Report and Written Opinion for International Application No. PCT/US2010/051678, mailed Apr. 14, 2011, 8 pages.
Office Action for U.S. Appl. No. 12/547,716, mailed Apr. 2, 2012, 11 pages.
Office Action for U.S. Appl. No. 12/528,253, mailed Mar. 21, 2012, 9 pages.
Office Action for U.S. Appl. No. 12/758,747, mailed Apr. 10, 2012, 11 pages.
Ex Parte Quayle Action in U.S. Appl. No. 29/376,026, mailed Apr. 30, 2012, 10 pages.
Office Action for U.S. Appl. No. 12/919,255, mailed May 25, 2012.
Office Action for U.S. Appl. No. 13/323,010, mailed Aug. 14, 2012.
First Office Action for Chinese Application No. 200880128908.3 mailed Apr. 24, 2012.
Association of Surgical Technologists, "AST Recommended Standards of Practice for Surgical Drapes," effective Apr. 13, 2008.
Ashar, Tom, "Ultrasound Guidance for Placement of Central Venous Catheters," Israeli Journal of Emergency Medicine, vol. 7, No. 2, Jun. 2007.
Buckner, C., et al., "Real-Time Sonography wth Electromagnetic Tracking Navigation for Biopsy of a Hepatic Neoplasm Seen on on Arterial Phase Computed Tomography," J Ultrasound Med 2011, 30:253-256.
"GE Heathcare: Ultrasound Imaging Accessories, vol. 6," CIVco Medical Solutions, Multi-Modality Imaging, 2011.
"Guiding Star with the LIDIS module," Ekliptik, 2007.
Ekliptik, LIDIS module, brochure, 2010.
Brochure for GE Healthcare Drapes and Sterile Covers, accessed on Jun. 21, 2012, at http://www.gehealthcare.com/usen/xr/surgery/docs/SurgeryDrapes&Film.pdf.
Ekliptik, "User Manual: Guiding Star/LIDIS," Jun. 16, 2010, reprinted from http://www.ekliptik.si/html/downloads/documents/manuals/LIDIS_user_manual.pdf.
Medtronic, "Orthopaedic Navigation Soluations," 2005, reprinted from http://behzadisportsdoc.com/wordpress/wp-content/uploads/2011/05/medtronic_orthonaysolutions.pdf.
GE Healthcare, "Interventional X-ray, OEC C-arm," 2012.
Office Action for U.S. Appl. No. 13/123,792, mailed Sep. 14, 2012.
Office Action for U.S. Appl. No. 12/528,253, mailed Aug. 16, 2012.
International Search Report and Written Opinion for International Application PCT/US2012/022481, mailed Jul. 31, 2012.
Office Action for U.S. Appl. No. 12/547,716, mailed Sep. 18, 2012.
Office Action for U.S. Appl. No. 13/323,010, mailed Jun. 4, 2013.
Office Action for U.S. Appl. No. 12/527,997, mailed May 21, 2013.
International Search Report and Written Opinion for International Application No. PCT/US2012/041613, mailed Feb. 15, 2013.
International Search Report and Written Opinion for International Application No. PCT/US2013/027042, mailed Jun. 12, 2013.
Office Action for U.S. Appl. No. 13/123,792, mailed Jul. 2, 2013.
Communication Pursuant to Article 94(3) EPC for European Application No. 07757660.1, mailed Jun. 5, 2013.
Decision of Rejection for Japanese Application No. 2009-551851, mailed Jun. 11, 2013.
Communication Pursuant to Article 94(3) EPC for European Application No. 08730964.7, mailed Jun. 6, 2013.
Notice of Reasons for Rejection for Japanese Application No. 2012-508518 mailed Dec. 10, 2013.
Office Action in Russian Application No. 2011146914, mailed Dec. 16, 2013.
Notice of Reasons for Rejection for Japanese Application No. 2012-508611, mailed Jan. 28, 2014.
'Innomed Hip Instruments—hohmann retractors,' reprinted from http://www.innonned.net/hip_rets_hohmanns.htm on Jan. 6, 2011, 8 pages.
Office Action for Russian Application No. 2011146669/14 mailed Apr. 3, 2014, 5 pages.
Office Action for U.S. Appl. No. 12/768,689, mailed Jul. 9, 2014.
First Office Action for Chinese Application No. 201080028779.8 mailed May 23, 2014.

* cited by examiner

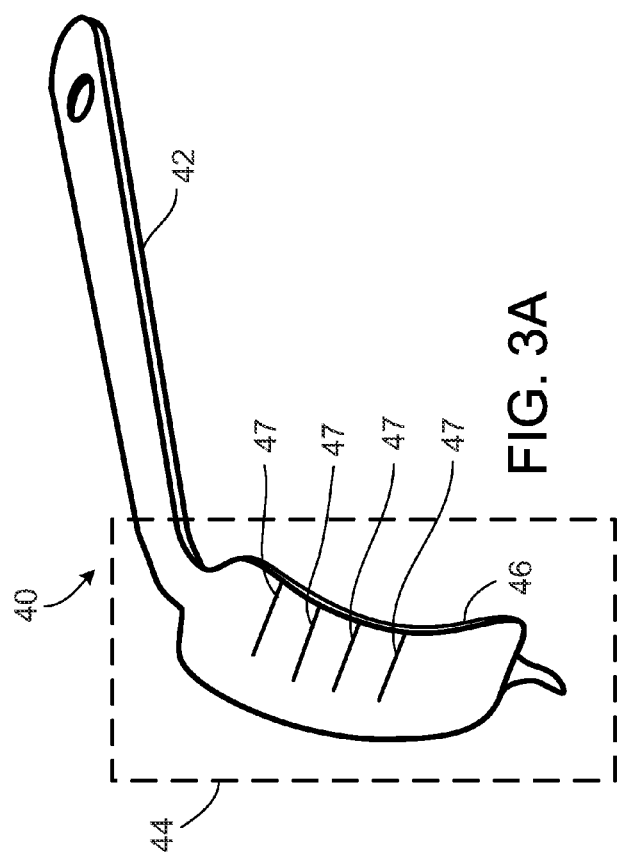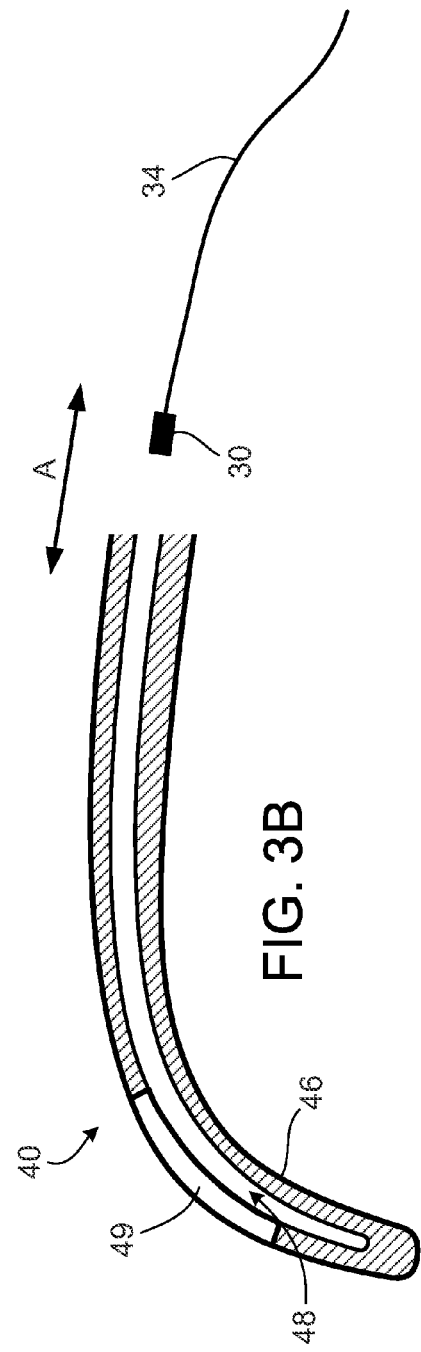

TARGETING OPERATION SITES

CROSS-REFERENCE TO RELATED APPLICATION

This application claims priority to and the full benefit of U.S. Provisional Application Ser. No. 61/436,047, filed Jan. 25, 2011, and titled "Targeting Operation Sites," the entire contents of which are incorporated herein by reference.

TECHNICAL FIELD

This disclosure relates to targeting operation sites.

BACKGROUND

Abnormalities of the hip socket and associated cartilage are often treated by surgical intervention. One such abnormality is femoroacetabular impingement (FAI), a condition of the hip joint in which rubbing of the femoral head and acetabulum damages the hip joint. FAI often damages the articular cartilage of the femoral head or of the acetabulum or damages the labral cartilage on and around the acetabular rim.

Although arthroscopy can be used to treat some abnormalities of the hip joint, its use is limited, and treatment of many abnormalities commonly involves distraction or dislocation of the hip. In many instances, an open surgical technique involves dislocation of the femoral head from the hip socket to expose all parts of the joint.

SUMMARY

In a general aspect, a system includes an identifier that produces electromagnetic fields, an implement that includes an electromagnetic field sensor, and a control unit configured to determine the position of a tool relative to an operation site of a joint. The implement is configured to be inserted into the joint without dislocating the joint, and to protect a bone of a joint when the operation site is accessed.

In another general aspect, a system for targeting an operation site includes an identifier having an electromagnetic field generator configured to produce electromagnetic fields. The system includes an implement that includes a handle, a blade portion, and an electromagnetic field sensor coupled to the blade portion. The electromagnetic field sensor is configured to produce a signal responsive to electromagnetic fields produced by the electromagnetic field generator. The system includes a control unit configured to access information indicating a position of the electromagnetic field sensor relative to the operation site, receive a signal from the electromagnetic field sensor that is indicative of a position of a tool relative to the electromagnetic field sensor, and determine a position of the tool relative to an operation site based on the received signal and the position of the electromagnetic field sensor relative to the operation site.

Implementations may include one or more of the following features. The control unit is further configured to compare a position of the tool to an acceptable range of axes for drilling to the operation site, and determine, based on the comparison, that the position of the tool relative to the operation site corresponds to an acceptable position within the range of axes for drilling to the operation site. The control unit is further configured to output on a graphical user interface an indication that the position of the tool relative to the operation site is acceptable. To compare a position of the tool to an acceptable range of axes for drilling to the operation site, the control unit is configured to compare the position of the tool to a range of axes for drilling through the ilium to reach an acetabular operation site. The control unit is configured to determine a distance between a tip of the tool and the operation site based on the received signal, and output, on a user interface, the determined distance. The control unit is configured to identify a plurality of linear paths that extend to the operation site through the pelvis and satisfy one or more predetermined criteria for acceptability, and output information that identifies the plurality of linear paths. The control unit is configured to receive information indicating selection of one of the plurality of linear paths, determine the position of the tool relative to the selected linear path, and output information that indicates the position of the tool relative to the selected linear path.

The electromagnetic field sensor is removably coupled to the implement, and wherein the implement defines a channel configured to receive the electromagnetic field sensor. The channel extends through a portion of the blade portion. The implement comprises a landmark located at a known position of the blade portion. The electromagnetic field sensor is coupleable at any of a plurality of predefined positions within the channel. The implement comprises a plurality of landmarks, each of the plurality of landmarks corresponding to one of the plurality of predefined positions within the channel, the landmarks being visible at an exterior surface of the implement. The implement includes a substantially rigid translucent portion. The translucent portion is located over the channel such that the position of the sensor or a device coupled to the sensor is visible within the channel. The translucent portion is located on a convex side of the blade portion configured to face away from a femoral head when the implement is engaged to the femoral head.

In another general aspect, a method of targeting an operation site includes: identifying an operation site; positioning a blade portion of an implement at the operation site, the implement including an electromagnetic field sensor, the electromagnetic field sensor being positioned at a known position relative to the operation site; locating the operation site using an identifier, the identifier having an electromagnetic field generator, and the electromagnetic field sensor communicating with the electromagnetic field generator when locating the operation site; and targeting the operation site using the position of the electromagnetic field sensor.

Implementations can include one or more of the following features. For example, the operation site is an acetabular operation site and positioning the blade portion of the implement includes positioning the blade portion between an acetabulum and a femoral head. The acetabular operation site is a portion of one of the acetabulum, acetabular cartilage, or labral cartilage. Positioning an implement includes positioning a landmark of the implement at a known position relative to the operation site, the position of the landmark being known relative to the position of the electromagnetic field sensor, and targeting the operation site includes targeting the operation site using the position of the electromagnetic field sensor and the position of the landmark. Positioning the implement between an acetabulum and a femoral head includes positioning the electromagnetic field sensor of the implement between the acetabulum and the femoral head. Targeting an acetabular operation site includes orienting an axis for drilling that extends through a portion of the ilium and the operation site. Targeting an operation site includes identifying a path to the operation site. Targeting an operation site includes identifying a plurality of paths to the operation site, each path extending linearly between the operation site and a different point on the surface of a tissue surrounding the operation site; and selecting, from the plurality of paths, a particular path to use as an axis for drilling that minimizes disturbance of tissue surrounding the operation site. The method includes drilling a cannula to the operation site. Drilling a cannula to the operation site includes drilling to a portion of the implement. Identifying the operation site includes visually locating the operation site.

In another general aspect, an implement for use in targeting an operation site includes: a handle, a blade portion coupled to the handle, and an electromagnetic field sensor coupled to the blade portion.

Implementations can include one or more of the following features. For example, the electromagnetic field sensor is fixedly coupled to the implement. The electromagnetic field sensor is removably coupled to the implement, and the implement defines a channel configured to receive the electromagnetic field sensor. The channel extends through a portion of the blade portion. The electromagnetic field sensor can be coupled at one of a plurality of predefined positions within the channel. The implement includes a landmark located at a known position of the blade portion. The landmark is positioned at a known offset from the sensor. The landmark is a visual indicator. The implement includes a substantially rigid translucent portion. The blade portion is shaped to conform to a femoral head. The blade portion includes a concave section. The blade portion includes a curved portion.

In another general aspect, an implement for use in targeting an operation site includes a handle, a blade portion coupled to the handle, the blade portion comprising a curved portion, and an electromagnetic field sensor removably coupled to the blade portion. The implement defines a channel that extends through a portion of the blade portion and is configured to receive the electromagnetic field sensor. The blade portion includes a transparent or translucent portion near the channel.

In another general aspect, a method of confirming acceptable positioning of a tool relative to an operation site includes: receiving a signal from a sensor coupled to an implement, the signal being indicative of a position of the tool relative to the sensor, a blade portion of the implement being positioned at the operation site; determining the position of the tool relative to the operation site using a known position of the sensor relative to the operation site; comparing the position of the tool to an acceptable range of axes for drilling to the operation site; determining that the position of the tool relative to the operation site corresponds to an acceptable position within the range of axes for drilling to the operation site; and outputting on a graphical user interface an indication that the position of the tool relative to the operation site is acceptable.

Implementations can include one or more of the following features. For example, the signal from the sensor is further indicative of a position of the tool relative to a landmark of the implement, the position of the landmark relative to the operation site being known, and determining the position of the tool relative to the operation site includes determining the position of the tool relative to the operation site using a known position of the sensor relative to the landmark and the known position of the landmark relative to the operation site. The operation site is an acetabular operation site and the axes for drilling include axes for drilling through the ilium to reach the blade portion of the implement that is positioned between the acetabulum and the femoral head.

In another general aspect, a system for targeting an operation site includes: an identifier having a guide and an electromagnetic field generator configured to produce electromagnetic fields; an implement including a handle, a blade portion, and an electromagnetic field sensor coupled to the blade portion, the electromagnetic field sensor configured to produce a signal responsive to electromagnetic fields produced by the electromagnetic field generator; and a control unit configured to receive a signal from the electromagnetic field sensor, and determine a position of the guide relative to an operation site based on the received signal and a known position of the electromagnetic field sensor relative to the operation site.

The details of one or more implementations are set forth in the accompanying drawings and the description below. Other features, objects, and advantages of the disclosure will be apparent from the description and drawings, and from the claims.

BRIEF DESCRIPTION OF THE DRAWINGS

FIG. 3A is a perspective view of an implement of the system of FIG. 1.

FIG. 3B is a cutaway view of the implement.

DETAILED DESCRIPTION

A system for targeting an operation site of a hip joint includes an identifier that is attachable to an orthopaedic tool and that includes an electromagnetic field generator operable to generate an electromagnetic field having known properties. The system also includes one or more electromagnetic sensors for attachment to an implement that may be used during surgery. The system includes a control unit to drive the electromagnetic field generator, receive output signals from the sensor(s), and display relative positions of the implement and the identifier. For example, the identifier, sensors, and control unit can include features as described in WIPO International Publication Nos. WO2008/106593 and WO2009/108214, and as described in U.S. patent application Ser. Nos. 12/758, 747 and 12/768,689, each of which is incorporated herein by reference in its entirety.

Figure 1:
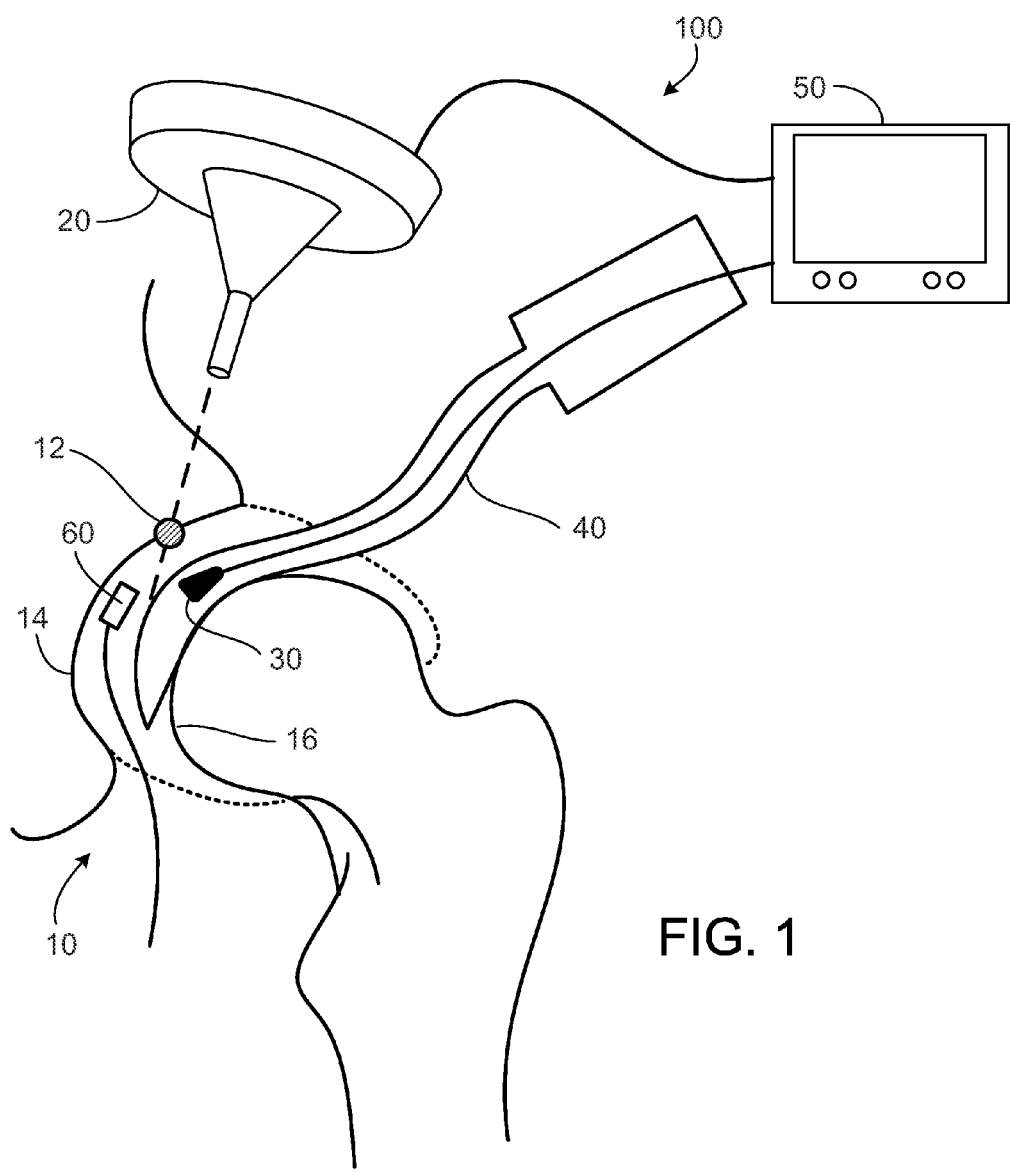
FIG. 1 is an illustration of a system for targeting an operation site.

Referring to FIG. 1, a system 100 is used to target an operation site 12 of a hip joint 10. The system 100 includes an identifier 20, an electromagnetic field sensor 30, an implement 40, and a control unit 50. The system 100 also includes an arthroscopic camera 60. The operation site 12, for example, is a defect of the acetabulum 14. As examples, the operation site 12 can be a region of the acetabulum 14, labral cartilage, acetabular cartilage, other tissue of the hip joint 10, and portions of the ilium other than the acetabulum 14.

Figure 2:
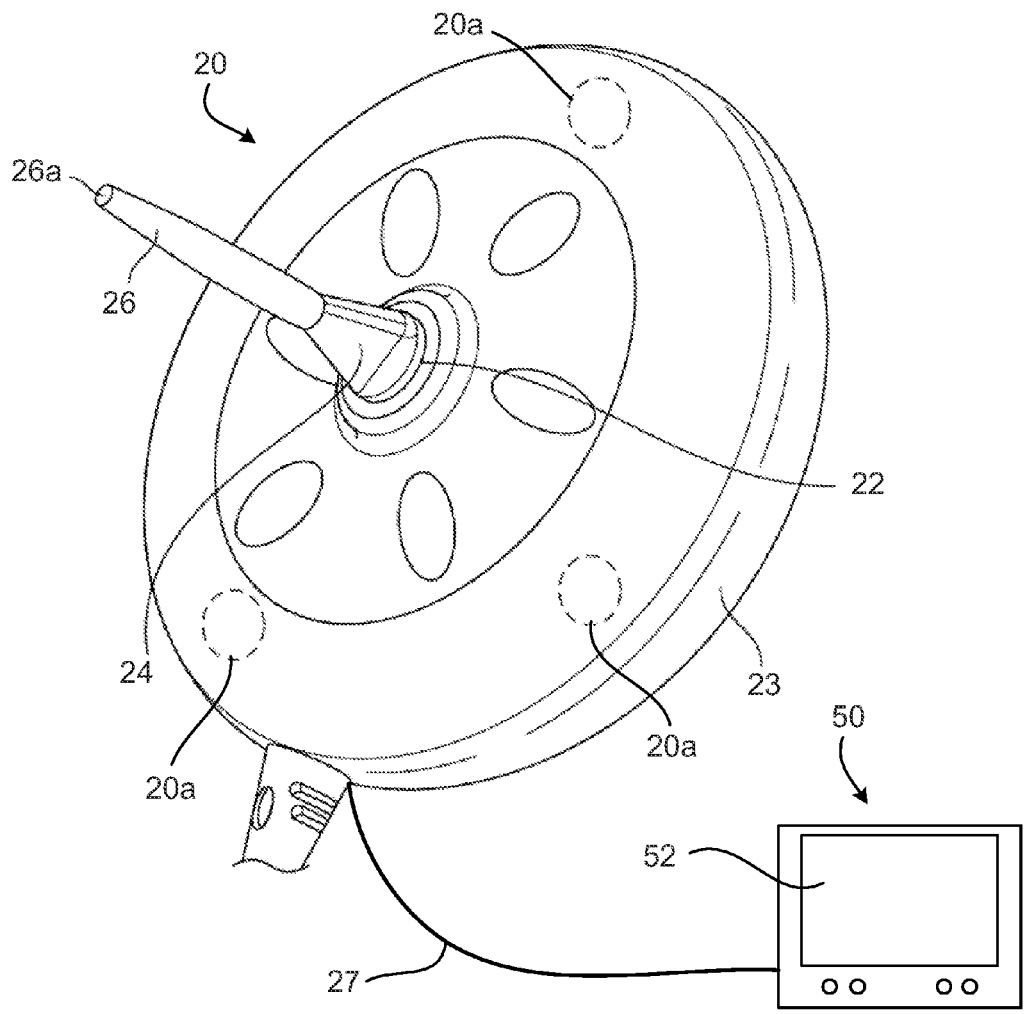
FIG. 2 is a perspective view of an identifier and a control unit of the system of FIG. 1.

Referring to FIG. 2, the identifier 20 includes an electromagnetic field generator 20a that produces an electromagnetic field that has known characteristics. The electromagnetic field generator 20a is located within a housing 23 of the identifier 20. The electromagnetic field generator 20a includes one or more coils or other components that produce electromagnetic fields. The generated electromagnetic fields are detected by one or more electromagnetic field sensors 30, and, based on the output of the sensor 30, the position (including the location and the orientation) of the sensor 30 relative to the identifier 20 is determined.

The useful range of the identifier 20 is a three-dimensional region around the identifier 20, referred to as the working volume of the identifier 20. The size and shape of the working volume is based on the characteristics of the electromagnetic fields produced by the electromagnetic field generator 20a and can be modified to be larger or smaller based on the need for targeting accuracy.

In some implementations, the working volume is a volume that surrounds the identifier 20. For example, the identifier 20 can be generally centrally located within the working volume. The working volume for some implementations, such as those used for targeting an acetabular operation site, can extend approximately 50 cm or more in width and approximately 40 cm or more in depth and be located at a distance of about 5 cm from the identifier 20. A drill guide, for example, will have a length of more than 5 cm to ensure that it is positioned within the working volume. Alternatively, for some uses, a working volume with smaller dimensions may be used to increase precision and accuracy.

The electromagnetic field sensor 30 communicates with the electromagnetic field generator of the identifier 20, for example, by receiving electromagnetic fields produced by the electromagnetic field generator when the electromagnetic field sensor 30 is located within electromagnetic communication with the electromagnetic field generator or within the working volume of the electromagnetic field generator of the identifier 20. When the electromagnetic field sensor 30 is located within the working volume of the identifier 20, the sensor 30 is able to generate output signals that indicate strength or intensity of the electromagnetic field generated by the identifier 20. The output signals can be used to accurately determine a location and orientation of the identifier 20 relative to the sensor 30. A sensor 30 located outside the working volume of the identifier 20, on the other hand, may not receive adequate electromagnetic energy from the identifier 20 to generate output signals that can be used to accurately determine the position of the identifier 20. The shape and size of the working volume of the identifier 20 depends in part on the configuration of the electromagnetic field generator 20a, specific characteristic of the operation of the electromagnetic field generator 20a, such as characteristics of a driving signal, and other factors.

An operator, such as a surgeon, can grip the identifier 20 by the housing 23 to position the identifier 20 relative to a patient, an implement, and/or a sensor, such as the electromagnetic field sensor 30. The identifier 20 can also include a coupling member 22 to which tools and other attachments are coupled. Using the coupling member 22, tools and other devices can be attached or guided by the identifier 20. For example, the coupling member 22 can receive a drill guide attachment 24 coupled to a drill guide 26. The identifier 20 is used to position the drill guide 26 so that a drill bit inserted through the drill guide 26 is guided to the position required by or appropriate for a medical procedure.

The identifier 20 can include a wired or wireless link to the control unit 50 to receive power and control signals to control the operation of the electromagnetic field generator 20a. For example, the identifier 20 can include a cable 27 that provides a connection to the control unit 50.

The control unit 50 controls the operation of the identifier 20 and receives inputs from one or more sensors 30. The control unit 50 also includes a user interface 52 that provides information to an operator of the system 100. The control unit 50 includes a processor that is configured to determine the location and orientation of the identifier 20 relative to the operation site 12 based on the input from the sensor 30 and information regarding the signal that controls the electromagnetic field generator 20a. The determination is made based on a known positional relationship between the sensor 30 and the operation site 12 and a determined position of the identifier 20 relative to the sensor 30.

The control unit 50 receives a signal that indicates a position of the identifier 20 relative to the operation site 12. For example, the signal can be received from the sensor 30. Using the signal from the sensor 30, the control unit 50 determines the position of the tool relative to the sensor 30. The control unit 50 also compares the position of the tool to an acceptable range of positions, such as a set of acceptable paths for drilling to the operation site 12.

In some implementations, the control unit 50 outputs on the user interface 52 an indication that the position of the identifier 20 relative to the operation site 12 or a landmark of the implement 40 is acceptable. For example, the output on the user interface 52 can include one or more elements, such as an element representing the angle of the identifier 20 relative to an axis to the operation site 12, one or more elements representing acceptable positions of the identifier 20 relative to the operation site 12, one or more elements representing unacceptable positions of the identifier 20 relative to the operation site 12, a numeric representation of the angle of the identifier 20 relative to one of the paths 64a-64c (FIGS. 7A, 7B), an element indicating that the current position of the identifier 20 is acceptable, a graphical representation of an acceptable conical range for drilling to the operation site 12, and an element indicating that the current position of the identifier 20 is unacceptable.

In some implementations, an electromagnetic field generator separate from the identifier can be used. For example, an identifier may be used that does not include an electromagnetic field generator. For example, an electromagnetic field generator can be a standalone unit or can be mounted to a chassis. The identifier can include an electromagnetic sensor that communicates with the electromagnetic field generator. A control unit can receive output signals of both the electromagnetic sensor of the identifier and the electromagnetic field sensor 30 coupled to the implement 40. The control unit can determine position of the identifier relative to the implement 40 based on the signals of the two electromagnetic field sensors. Additional sensors can also be used. Additional details of this implementation are described in WIPO International Publication Nos. WO2008/106593 and WO2009/108214, and in U.S. patent application Ser. Nos. 12/758,747 and 12/768,689, each of which, as noted above, is incorporated herein by reference in its entirety.

Now referring to FIG. 3A, the implement 40 includes a handle 42 and an insertable portion 44. The insertable portion 44 is shaped to engage a portion of the femoral head 16 when the insertable portion 44 is inserted into the hip joint 10, for example, between the acetabulum 14 and a femoral head 16. A surgeon uses the handle 42 to place the insertable portion 44 in the hip joint 10 and to position the insertable portion 44 and/or a sensor 30 relative to the operation site 12.

The engagement of the insertable portion 44 and the femoral head allows the insertable portion 44 to act as a barrier to protect the femoral head from damage during surgery. The insertable portion 44 includes one or more blade portions 46 configured to contact a portion of the femoral head 16. The blade portion 46 can be, for example, substantially flattened, and can also be shaped to conform to the surface of the femoral head. For example, the blade portion 46 can include a curved portion that is curvilinear along a portion of the length of the blade portion 46. The blade portion 46 can include a concave or spoon-like portion to fit closely to the femoral head, even when the blade portion 46 is substantially flattened. The blade portion 46 may also be flexible to facilitate positioning in the hip joint 10, and to improve conformance to the femoral head 16. In some implementations, the blade portion 46 can have a curvature at some portions that generally corresponds to a diameter of approximately 40-60 mm. The blade portion 46 can be wide enough to protect the femoral head from damage and narrow enough to avoid obscuring visualization of the operating site.

A surgeon can position the insertable portion 44 in the hip joint 10 so that a portion of the insertable portion 44 has a known location relative to the operation site 12. For example, a surgeon can use an arthroscopic camera 60 to locate a defect of the acetabulum 14, and the surgeon can position the insertable portion 44 at a known position relative to the defect. As an example, while viewing the defective area of the acetabulum 14 using the arthroscopic camera 60, the surgeon can bring the insertable portion 44 into the viewing area of the arthroscopic camera 60. In such an implementation, the insertable portion 44 can include one or more markings or landmarks 47 disposed on the insertable portion 44 at a fixed position so that the surgeon can align the one or more markings or landmarks 47 relative to the defective area.

In some implementations, a surgeon can use other techniques to place the insertable portion 44 at a known location relative to the operation site 12, such as one or more of direct visualization, X-ray imaging, magnetic resonance imaging (MRI), and computerized tomography (CT).

Referring to FIG. 3B, the sensor 30 can be positioned on or within the implement 40 at a number of different locations with respect to the implement 40. In some implementations, the sensor 30 is removably attached and/or positioned with respect to the implement 40. For example, the implement can define a channel 48 or other opening to receive the sensor 30, or a housing that includes the sensor 30. The channel 48 can extend through a portion of the insertable portion 44 so that the sensor 30 is positioned within the insertable portion 44. In some instances, positioning the sensor 30 near the operation site 12 can increase the accuracy of determining the position of the operation site 12.

The sensor 30 includes, for example, an inductive sensor that is configured to respond to an electromagnetic field produced by the identifier 20 by outputting one or more induced electrical currents. The sensor 30 is capable of producing signals that allow the position of the identifier 20 to be determined. For example, the sensor 30 can include two or more inductive coils that each outputs an induced electrical current. The outputs of the sensor 30 allow determination of the location and orientation of the sensor 30 in up to six degrees of freedom, such as along three translational axes, generally called X, Y, and Z, and three angular orientations, generally called pitch, yaw, and roll, which are defined as rotation about the three translational axes.

The sensor 30 includes a connection to transmit the output signals, or data related to the signals. For example, a sensor lead 34 provides a wired connection for transmission of an output of the sensor 30. The sensor lead 34 can carry signals produced by the sensor 30 in response to electromagnetic fields. In some implementations, the connection can include a wireless transmitter. Additionally, the sensor lead 34 can include more than one connection, and the sensor lead 34 can carry power and control signals in addition to signals or data, and bi-directional communication is possible. For example, information regarding calibration of the sensor 30 can be stored in a storage device coupled to the sensor 30.

In some implementations, the sensor 30 can be coupled to the implement 40 at one of several positions relative to the implement 40. For example, the sensor 30 can move along the channel 48 (as indicated by arrow A in FIG. 3B) to be positioned at one of multiple positions along the length of the channel 48. The positions along the channel 48 can be discrete positions or positions along a continuous range. The sensor 30 can be coupled to the implement 40 at a known position of the implement 40, and the known position can be maintained during targeting of the operation site 12. Part of or all of the channel 48 can be an internal channel within the implement 40.

In some implementations, the position of the sensor 30 relative to the implement 40 can be visibly determined. For example, the implement 40 can include a transparent or translucent portion 49 located at the insertable portion 44, for example, at the blade portion 46 of the insertable portion 44. The translucent portion 49 can be located near (e.g., at or over) a section of the channel 48 so that the position of the sensor 30 (or the housing that includes the sensor 30 or other device coupled to the sensor 30) is visible through the translucent portion 49 when the sensor 30 is located within a particular range of positions within the channel 48. The translucent portion 49 can be located at a portion of the channel 48 that is viewable at the side of the implement 40 that does not contact the femoral head 16. For example, the translucent portion 49 can be located on the blade portion 46, at a convex outer surface of the blade portion. For example, the translucent portion 49 is configured to face away from the femoral head when the implement 40 is engaged to the femoral head.

As noted above, the insertable portion 44 can also include features that facilitate positioning of the insertable portion 44 relative to the operation site 12. For example, the insertable portion 44 includes one or more landmarks 47 that are used as a reference point of the implement 40. As examples, a landmark may be a structure, a void, a boss, a channel, a detent, a flange, a groove, a member, a partition, a step, an aperture, a bore, a cavity, a dimple, a duct, a gap, a notch, an orifice, a passage, a slit, a hole, a marking, or a slot. The landmark 47 can be visibly discernible from the exterior of the insertable portion 44, for example, the landmark 47 is visible at a side of the blade portion 46 that does not contact the femoral head 16 so that the surgeon can position the landmark 47 relative to the operation site 12

In some implementations, the sensor 30 is fixed to the implement 40 at a known position relative to the insertable portion 44, to another portion of the implement 40, or relative to a landmark 47 of the insertable portion 44. For example, the sensor 30 can be located at a landmark 47 or at a known offset distance from a landmark 47.

Whether the sensor 30 is fixed to the implement 40 or removably attached to the implement 40, the position of the sensor 30 relative to the implement 40 is known at the time the operation site 12 is targeted. The position of the sensor 30 relative to the implement 40 is maintained during targeting, but can change if the surgical procedure or surgeon requires a change. Because the shape and dimensions of the implement 40 are known, and because the sensor 30 is maintained at a known position relative to the implement 40, the position of the sensor 30 can be used to determine the position of the operation site 12 when the implement 40 is positioned at a location relative to the operation site 12.

FIGS. 4-6, 7A, and 7B illustrate a process for targeting an operation site 12 of the hip joint 10. During surgery, the precise location and orientation of the operation site 12 may be needed, for example, to correctly position a drill bit or other device. Access to the operation site 12 from within the hip joint 10 may be very limited unless the hip joint 10 is dislocated. Using the identifier 20 and a sensor 30 located at a known location relative to the operation site 12, permits a surgeon, for example, to target the operation site 12 from outside the hip joint 10, through the pelvis and surrounding tissue. Targeting in this manner provides access to the operation site 12 without requiring dislocation of the hip joint 10. As a result, the operation site 12 can be accessed without incurring the trauma and difficulty associated with dislocating the hip joint 10.

Figure 4:
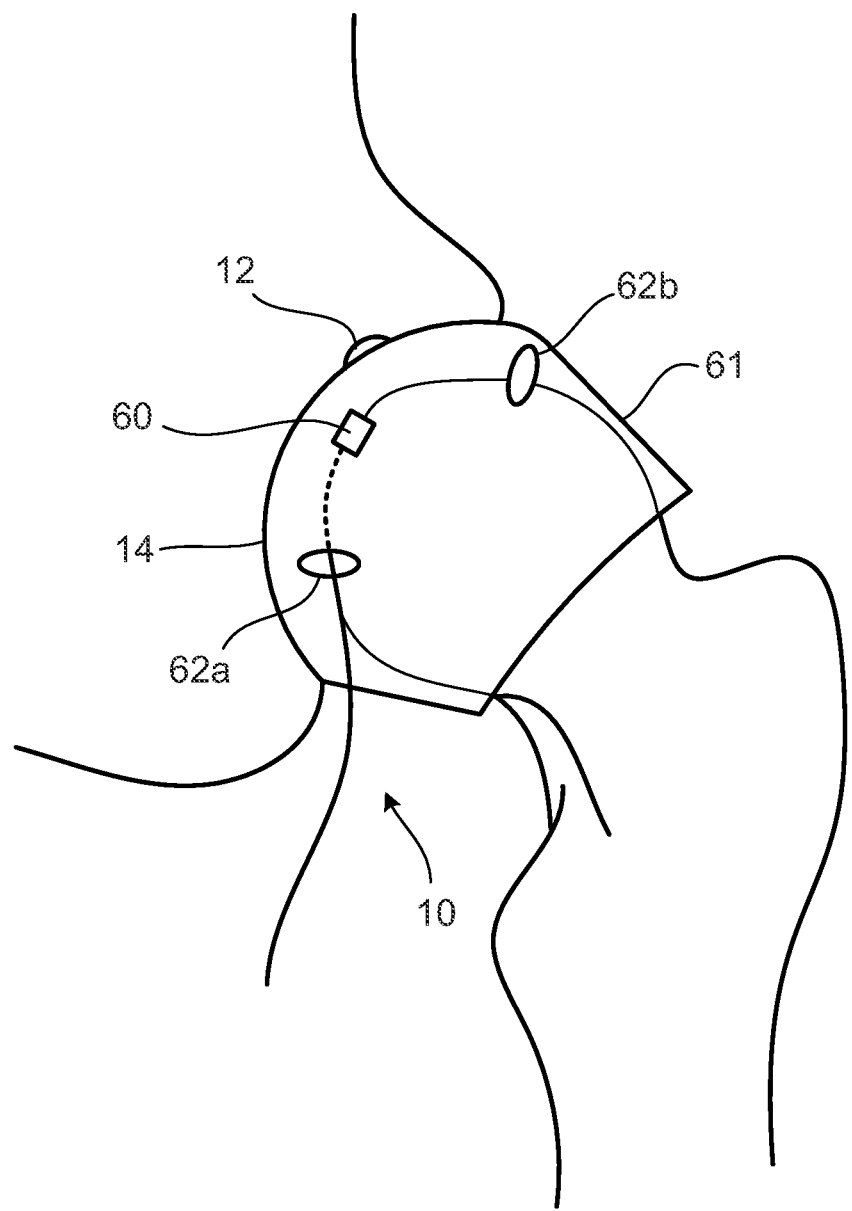
FIGS. 4-6, 7A, and 7B are illustrations of a process for targeting an operation site.

Referring to FIG. 4, one or more incisions are made in the capsule 61 of the hip joint 10 to create access ports 62a, 62b. The arthroscopic camera 60 may be inserted into the capsule 61 through the access port 62a, and tools, such as tools used for cutting or scraping or guides for other tools, may be inserted into the capsule 61 through the access port 62b. Other access ports may be made in the capsule 61 to allow fluid to be pumped into the hip joint 10 or waste fluid to be removed from the hip joint 10. Images from the camera 60 may be used to identify and locate an operation site 12, for example, a defect in the bone or cartilage of the hip joint 10. Minor abnormalities of the hip joint 10 may be corrected endoscopically through the access ports. Other conditions, however, may require more significant access. Images from the arthroscopic camera 60 are used to identify and locate an operation site 12, for example, the site of a defect that may not be treatable by endoscopy.

Figure 5:
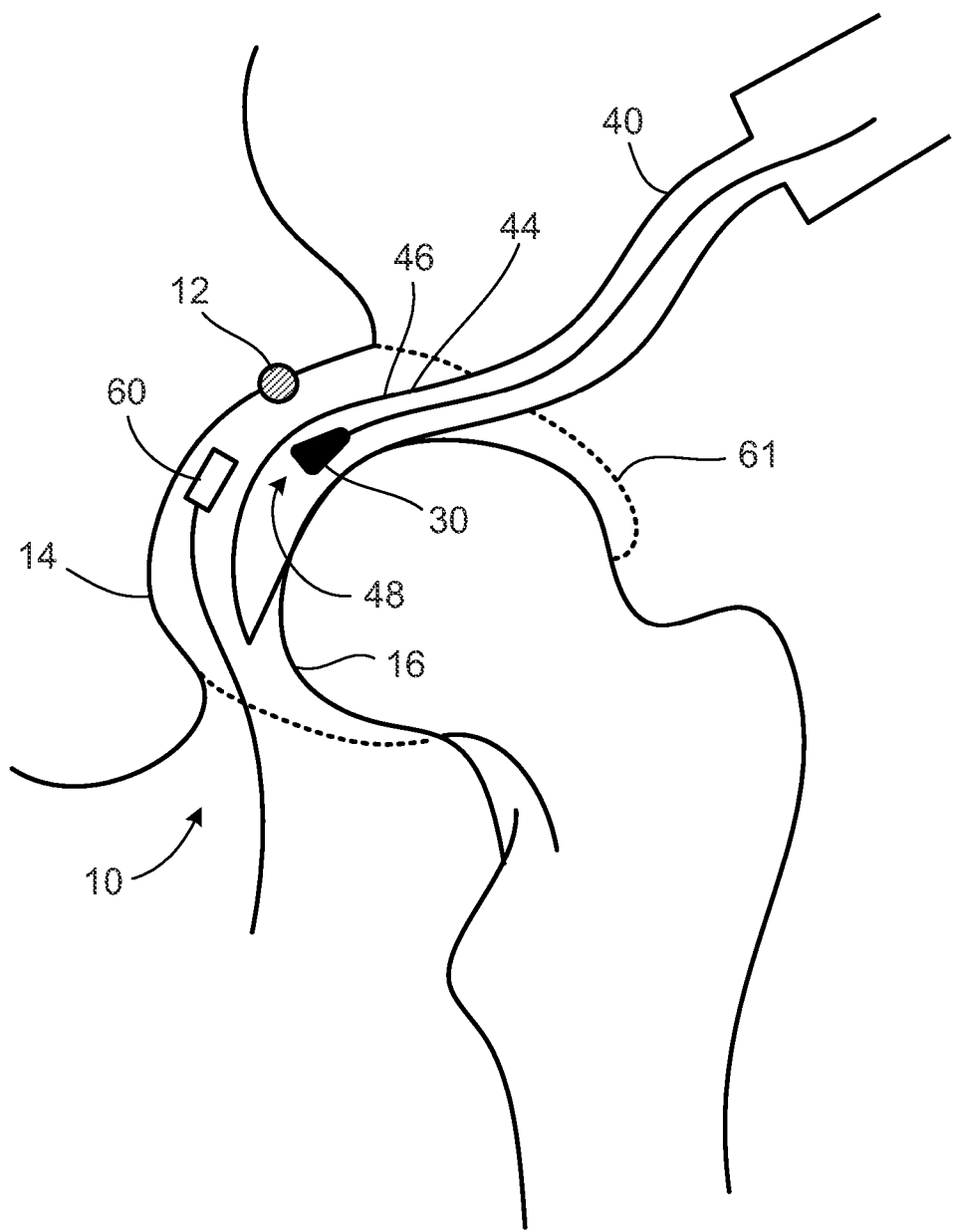

Referring to FIG. 5, the implement 40 is inserted into the capsule 61 through the access port 62b and positioned in the hip joint 10. For example, at least a portion of the insertable portion 44 of the implement 40 can be inserted into the hip joint 10. The blade portion 46 is positioned between the acetabulum 14 and the femoral head 16. Specifically, the blade portion 46 is positioned over the femoral head to contact the surface of the femoral head 16.

The insertable portion 44 of the implement 40 is positioned within the hip joint 10 so that the position of the implement 40 is known relative to the operation site 12. During the positioning of the implement 40, the arthroscopic camera 60 can be maintained in the hip joint 10 to facilitate placement of the implement 40. Images from the camera 60 can be used to locate a particular portion of the insertable portion 44, such as a landmark 47, at a known position relative to the operation site 12. For example, a landmark 47 of the insertable portion 44 can be located at or near to the operation site 12. The edges, end, or contours of the implement 40 can also be used to position the implement 40 relative to the operation site 12. The insertable portion 44 can be positioned relative to the operation site, and the operation site can be targeted and accessed as described below, without dislocating the hip joint 10.

Additionally, or alternatively, the position of the sensor 30 can be adjusted relative to the implement 40. For example, the sensor 30 can be moved to a portion of the channel 48 in proximity to the operation site 12. In one implementation, the sensor 30 can be moved along the channel 48 in the implement 40 to a position at or near the operation site 12. The position of the sensor 30 relative to the operation site 12 can be determined using images from the camera 60, for example, by viewing the position of the sensor 30 through the translucent portion 49 of the implement 40. Alternatively, as discussed above, one or more landmarks 47 can indicate the position of the implement 40 relative to the operation site 12, and the sensor 30 can be positioned at a known position out of several predefined positions relative to the implement 40. For example, a surgeon can position the sensor 30 at, or at a known offset from, one of the landmarks 47. Calibration of the sensor 30, if necessary, can be performed prior to inserting the implement 40 into the access port 62b.

Figure 6:
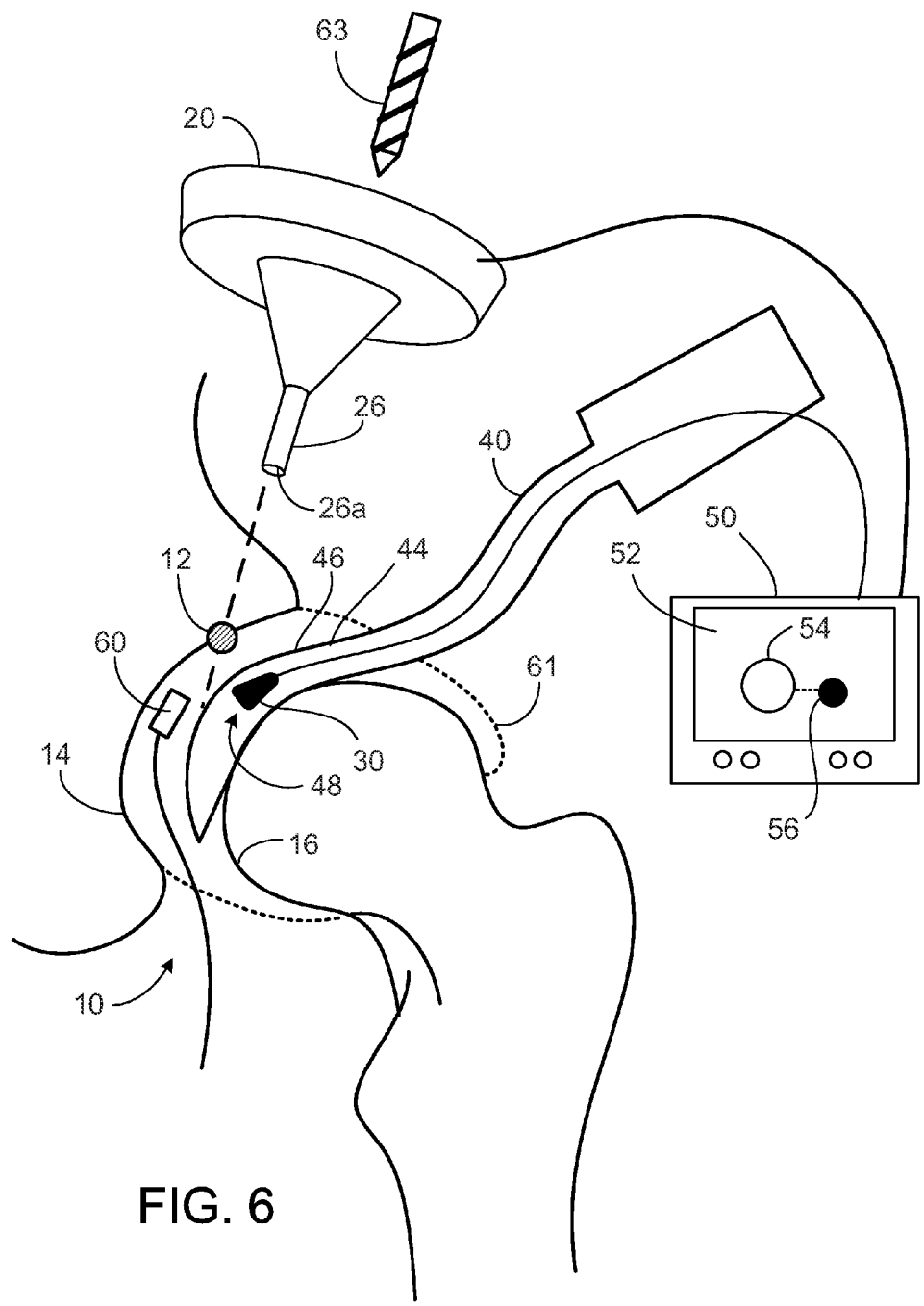

Referring to FIG. 6, the operation site 12 is targeted using the identifier 20. To target the operation site 12, the identifier 20 is positioned near the operation site 12, such as with a tip 26a of the drill guide 26 near the pelvis of the patient. When the sensor 30 is located within the working volume of the identifier 20, and the electromagnetic field generator 20a produces an electromagnetic field, the control unit 50 receives signals produced by the sensor 30 that indicate the position of the sensor 30 relative to the identifier 20. Using the signals from the sensor 30, the control unit 50 can determine the position of the identifier 20 relative to the operation site 12.

For example, in determining the position of the identifier 20 relative to the operation site 12, the control unit 50 can access information about the shape of the implement 40 and the location of the implement 40 relative to the operation site 12. This information can be input using the user interface 52 or another input mechanism. Additionally, the control unit 50 can access information regarding the location of the sensor 30 relative to the implement 40. For example, the sensor 30 can be attached at a pre-selected landmark 47 of the implement 40, or information regarding a landmark 47 of the implement 40 to which the sensor 30 is attached can be input to the control unit 50, such as by a user touching a portion of the interface 52 to indicate a landmark 47 near which the sensor 30 is attached. The signals of the sensor 30 can be used in combination with the information regarding known positions of the sensor 30 relative to the implement 40 and/or relative to the operation site 12 to determine the location and orientation of the identifier 20 relative to the operation site 12.

The control unit 50 outputs information about the position of the identifier 20 relative to the operation site 12 on the user interface 52. Based on the user interface 52, a surgeon or other operator can place the identifier 20 in a position where the interface 52 indicates that the tip 26a of the drill guide 26 is aligned along a linear axis to the operation site 12 (FIG. 6). In some implementations, the interface 52 includes a first identifier element 54, such as a first circle, that indicates a position of the distal tip 26a of the drill guide 26. Thus, when the first identifier element 54 is in alignment with a target identifier element 56 that corresponds to, and represents a targeted operation site 12, the interface 52 indicates that the tip 26a of the drill guide 26 is directly above the operation site 12 represented by the target identifier element 56. The interface 52 can also include different graphical elements, and can include audio or haptic outputs.

The control unit 50 can also output information that indicates a distance (e.g., drill depth) between, for example, the tip 26a of the drill guide 26 and the operation site 12. The distance can be a distance that reaches the operation site 12 based on the current position of the identifier 20 relative to the sensor 30. In some implementations, the control unit 50 can determine the distance by subtracting the length of the drill guide 26 (e.g., the distance between the tip 26a of the drill guide 26 and the identifier 20) from the distance between the identifier 20 and the sensor 30. The control unit 50 can also adjust the distance based on any offsets between the sensor 30 and the operation site 12, for example, based on the position of the sensor 30 relative to the operation site 12. The operator can use the distance information to drill a hole through the pelvis to the proper depth, for example, a depth that reaches the operation site 12 but does not damage surrounding tissue.

Figures 7A, 7B:
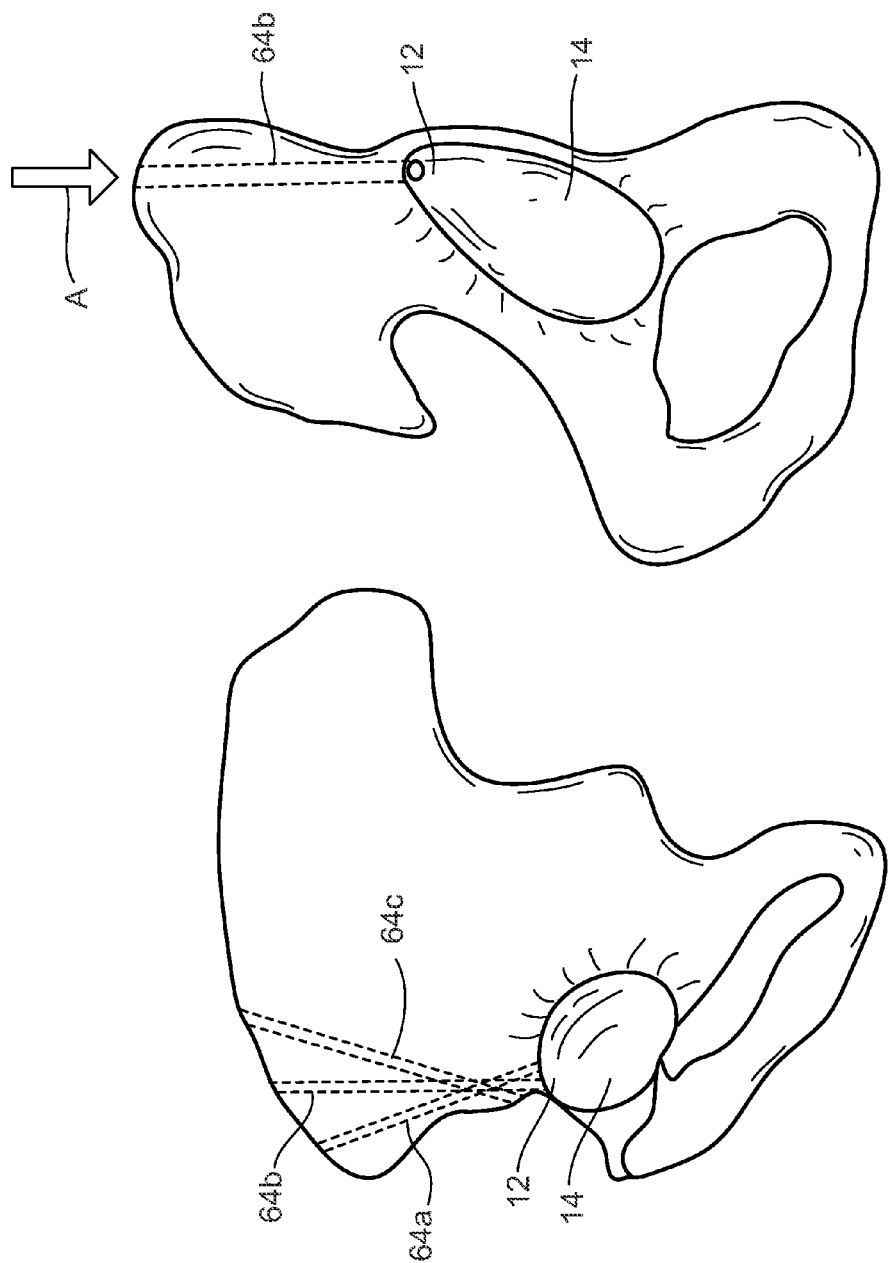

Referring to FIG. 7A, targeting the operation site 12 can include identifying one or more paths 64a-64c through the pelvis to the operation site 12. For example, the control unit 50 can identify multiple paths 64a-64c that traverse different portions of the pelvis. Information about the one or more paths 64a-64c can be output on the interface 52 of the control unit 50. For example, multiple possible axes for drilling (e.g., linear paths) can be displayed. In some implementations, each path 64a-64c can have the operation site 12 as an end point. Individual paths 64a-64c and/or ranges of paths (e.g., various angle ranges relative to the pelvis) can be determined.

The control unit can identify the paths 64a-64c to extend to the operation site 12 through the pelvis (e.g., through the ilium) and to satisfy one or more predetermined criteria for acceptability. For example, the control unit 50 can determine each of the paths 64a-64c to have acceptable positioning relative to the pelvis, for example, to intersect the pelvis at a predefined range of locations and to extend within predetermined angle ranges relative to the pelvis. The paths 64a-64c can thus be selected by the control unit 50 to provide different options for accessing the operation site 12, where each path 64a-64c meets a set of constraints defined to, for example, meet the requirements of the procedure and/or avoid unnecessary tissue damage.

Providing multiple paths 64a-64c may enable the surgeon or operator to select a path that minimizes the amount of tissue disturbed during the surgical procedure and may enable the surgeon to optimize recovery time and minimize trauma to the areas surrounding the operation site. The control unit 50 can also identify and indicate to the surgeon an optimized or suggested path to access the operation site 12. For example, referring to FIG. 7B, the control unit 50 can indicate that of the identified paths 64a-64c, a particular path 64b would minimize disturbance to the tissue surrounding the operation site 12. The control unit 50 can indicate the identified path based on, for example, program(s) stored in the control unit or previous user input to permit the program running on the control unit 50 to calculate the optimized path for accessing the operation site 12. The control unit 50 can select a suggested path based on one or more criteria, including, for example, deviation from one or more preferred, predetermined paths. Other criteria can include minimizing the distance through bone, avoiding drilling through bone below a threshold thickness, avoiding drilling within a threshold distance of the edge of a bone, avoiding drilling through particular tissues or anatomical features, and orienting the path to provide access at an angle or within an angle range that facilitates access by the surgeon.

After the control unit 50 outputs information that identifies the one or more paths 64a-64c, the operator can optionally use the user interface 52 to select one of the paths 64a-64c as the desired path to access the operation site 12. The control unit 50 can receive information indicating selection of one of the plurality of paths 64a-64c, and can determine the position of the tool, such as a drill or drill guide 26, relative to the selected path based on the signals from the sensor 30. The control unit 50 can output information that indicates the position of the tool relative to the selected path.

The control unit 50 can also confirm acceptable positioning of a tool, such as a drill or drill guide 26, relative to the operation site 12 based on the signals from the sensor 30. For example, the control unit 50 can indicate on the interface 52 whether the drill guide 26 of the identifier 20 is aligned with the selected path 64b. The control unit 50 can also output information about various measurements and angles to assist the operator to align a tool along an appropriate drilling axis. The position of a tool can be determined to be acceptable when, for example, an axis defined by the tool is located within a predetermined distance or angle of a selected path 64b. Alternatively, the position of a tool can be determined to be acceptable when, for example, an axis defined by the tool extends through or within a predetermined distance of the operation site 12, and has an orientation relative to the pelvis or surrounding tissue that is within a predetermined range of orientations. The predetermined range of orientations can be selected to provide an appropriate angle of access for the surgical procedure and avoid unnecessary tissue damage.

The interface 52 of the control unit 50 can also indicate a current angular position of the identifier 20 relative to the operation site 12 or a landmark 47 of the implement 40 to confirm acceptable positioning of a tool relative to the operation site 12. For example, the control unit 50 can display a current angle of the drill guide 26 relative to an operation site 12 so that an operator, such as a surgeon, can confirm that a hole drilled in the pelvis will result in minimal damage to the tissue surrounding the operation site 12. As illustrated in FIG. 6, as the first identifier element 54 and the target identifier element 56 approach one another on the interface 52, the angle of the identifier 20 approaches zero degrees from a reference axis, such as the axis of the selected path 64b to the operation site 12. Thus, when the first identifier element 54 and the target identifier element 56 are concentric, the identifier 20 is aligned to the selected path 64b.

When the identifier 20 and other tools are aligned relative to the operation site 12, the operator of the identifier 20 can drill a cannula to the operation site 12 along the selected path, in the direction indicated by arrow A in FIG. 7B. The cannula can be drilled through a portion of the pelvis (for example, through the ilium) to reach the operation site 12.

Referring to FIG. 6, a tool 63 can be inserted into the drill guide 26 to create a cannula to the operation site 12. The tool 63 can be, for example, a drill bit, a high speed burr, a reamer, or a broach. To protect the femoral head from damage, the insertable portion 44 of the implement 40 can remain in the hip joint 10 while drilling proceeds. The camera 60 can remain in the hip joint 10 to provide visual information about the operation site while drilling proceeds, as well as providing back-up confirmation of the drilling procedure. Because the insertable portion 44 of the implement 40 serves as a barrier, the operator can drill through the pelvis to the operation site 12 until the tip of the tool 63 contacts the insertable portion 44. After the cannula is created to access the operation site 12, the insertable portion 44 may be maintained in place while damaged or defective tissue is removed, or it may be removed prior to repairing the operation site 12 if the surgical procedure or surgeon requires it to be removed. Natural or synthetic materials can be used to repair the operation site 12 and the cannula.

Figure 8:
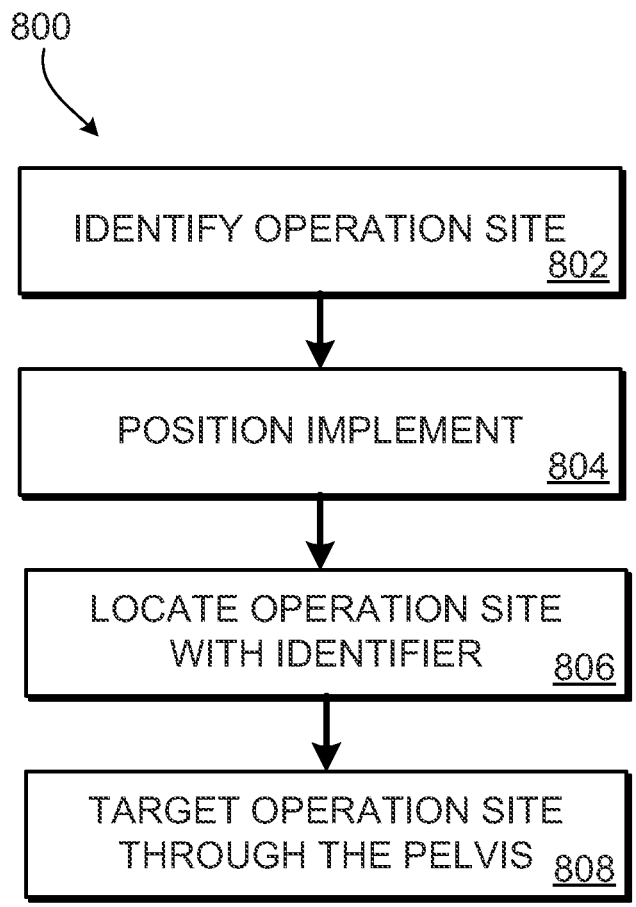
FIG. 8 is a flow diagram of a process for targeting an operation site.

Referring to FIG. 8, a process 800 for targeting an acetabular operation site includes identifying an operation site (802), for example, a portion of the acetabulum, acetabular cartilage or labral cartilage. The operation site can be identified visually using an arthroscopic camera.

The process 800 includes positioning an implement (804), for example, positioning an implement between an acetabulum and a femoral head. The implement can include an electromagnetic field sensor positioned at a known position relative to the operation site. This may be achieved by, for example, (i) maintaining the electromagnetic field sensor at a known position relative to the implement and moving the implement to a known position relative to the operation site, or (ii) moving the electromagnetic field sensor relative to the implement, which is fixed relative to the operation site.

The process 800 includes locating the operation site using an electromagnetic identifier that includes an electromagnetic field generator (806). The electromagnetic field sensor can be located within a working volume of the electromagnetic field generator when locating the operation site.

The process 800 includes targeting the operation site through the pelvis using the position of the electromagnetic field sensor (808). For example, a path to the operation site through the pelvis (for example, through the ilium) can be identified. The process 800 can also include drilling a cannula through the pelvis (for example, through the ilium), to the operation site.

Figure 9:
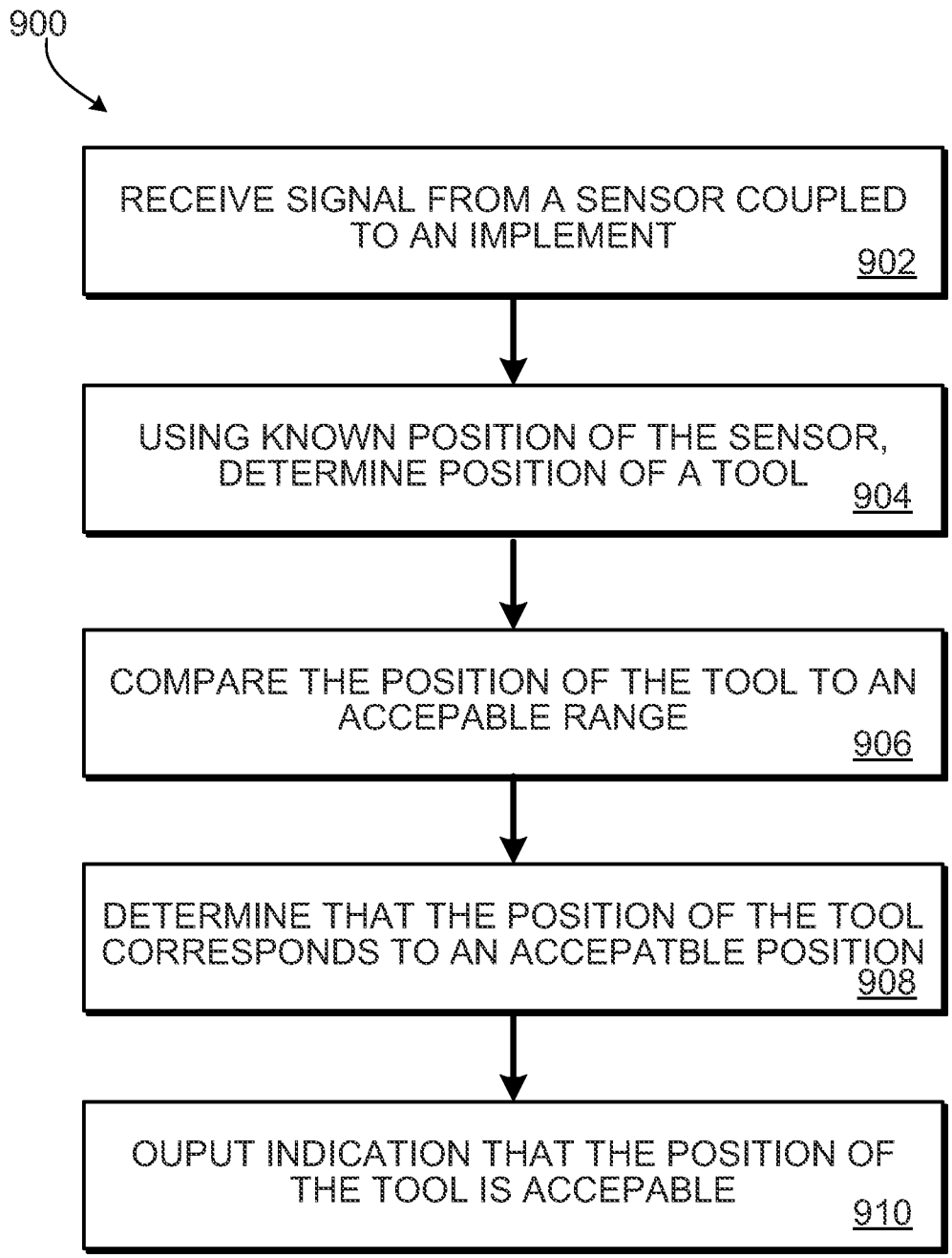
FIG. 9 is a flow diagram of a process for confirming the position of a tool relative to an operation site.

Referring to FIG. 9, a process 900 for confirming acceptable positioning of a tool (e.g., a drill guide, drill, reamer, or broach) relative to an acetabular operation site is illustrated. A signal is received from a sensor coupled to an implement (902), where the signal indicates the position of the tool relative to the sensor. A portion of the implement can be positioned between an acetabulum and a femoral head. The position of the tool relative to the operation site is determined using a known position of the sensor relative to the operation site (904). The position of the tool is compared to an acceptable range of axes for drilling to the operation site (906). The position of the tool can be an axis defined by the tool or the guide, for example, an axis through the center of a drill guide or an axis along the center of a drill bit. It is determined that the position of the tool corresponds to an acceptable position within the range of axes for drilling to the operation site (908). An indication that the position of the tool relative to the operation site is acceptable is output on a graphical user interface (910).

A number of implementations and alternatives have been described. Nevertheless, it will be understood that various modifications may be made without departing from the spirit and scope of the disclosure. For example, although some of the implementations above have been described with respect to targeting an acetabular operation site, for example, a portion of the acetabulum, acetabular cartilage or labral cartilage, or confirming acceptable positioning of a tool relative to an acetabular operation site, the above-described implementations may be employed for targeting other operation sites within a body, such as for example, the shoulder joint. Accordingly, other implementations are within the scope of the following claims.

The invention claimed is:

1. A system for targeting an operation site, comprising:
an identifier having an electromagnetic field generator configured to produce electromagnetic fields;
a surgical implement comprising:
a handle;
a blade portion coupled to the handle, the blade portion comprising a curved portion; and
an electromagnetic field sensor removably coupled to the blade portion,
the surgical implement defining a channel that extends through a portion of the blade portion and is configured to receive the electromagnetic field sensor, the blade portion including a transparent or translucent portion near the channel,
wherein the electromagnetic field sensor is coupleable at any of a plurality of predefined positions within the channel, and
wherein the surgical implement comprises a plurality of landmarks, each of the plurality of landmarks corresponding to one of the plurality of predefined positions within the channel, the landmarks being visible at an exterior surface of the surgical implement; and
a control unit configured to
access information indicating a position of the electromagnetic field sensor relative to the operation site,
receive a signal from the electromagnetic field sensor that is indicative of a position of a tool relative to the electromagnetic field sensor, and
determine a position of the tool relative to an operation site based on the received signal and the position of the electromagnetic field sensor relative to the operation site.

2. The system of claim 1, wherein the control unit is further configured to:
compare a position of the tool to an acceptable range of axes for drilling to the operation site; and
determine, based on the comparison, that the position of the tool relative to the operation site corresponds to an acceptable position within the range of axes for drilling to the operation site.

3. The system of claim 2, wherein the control unit is further configured to output on a graphical user interface an indication that the position of the tool relative to the operation site is acceptable.

4. The system of claim 2, wherein to compare a position of the tool to an acceptable range of axes for drilling to the operation site, the control unit is configured to compare the position of the tool to a range of axes for drilling through the ilium to reach an acetabular operation site.

5. The system of claim 1, wherein the control unit is configured to:
determine a distance between a tip of the tool and the operation site based on the received signal; and
output, on a user interface, the determined distance.

6. The system of claim 1, wherein the control unit is configured to:
identify a plurality of linear paths that extend to the operation site through the pelvis and satisfy one or more predetermined criteria for acceptability; and
output information that identifies the plurality of linear paths.

7. A surgical implement comprising:
a handle;
a blade portion coupled to the handle, the blade portion comprising a curved portion; and
an electromagnetic field sensor removably coupled to the blade portion,
the surgical implement defining a channel that extends through a portion of the blade portion and is configured to receive the electromagnetic field sensor, the blade portion including a transparent or translucent portion near the channel,
wherein the electromagnetic field sensor is coupleable at any of a plurality of predefined positions within the channel, and
wherein the surgical implement comprises a plurality of landmarks, each of the plurality of landmarks corresponding to one of the plurality of predefined positions within the channel, the landmarks being visible at an exterior surface of the surgical implement.

8. The surgical implement of claim 7, wherein the implement comprises a landmark located at a known position of the blade portion.

9. The surgical implement of claim 7, wherein the blade portion includes a concave section.

10. The surgical implement of claim 7, wherein the blade portion is shaped to conform to a femoral head.

11. A method of targeting an operation site, the method comprising:
identifying an operation site;
providing a surgical implement comprising:
a handle;
a blade portion coupled to the handle, the blade portion comprising a curved portion; and an electromagnetic field sensor removably coupled to the blade portion, the surgical implement defining a channel that extends through a portion of the blade portion and is configured to receive the electromagnetic field sensor, the blade portion including a transparent or translucent portion near the channel, wherein the electromagnetic field sensor is coupleable at any of a plurality of predefined positions within the channel, and wherein the surgical implement comprises a plurality of landmarks, each of the plurality of landmarks corresponding to one of the plurality of predefined positions within the channel, the landmarks being visible at an exterior surface of the surgical implement;

positioning a blade portion of the surgical implement at the operation site, the electromagnetic field sensor being positioned at a known position relative to the operation site;

locating the operation site using an identifier, the identifier having an electromagnetic field generator, and the electromagnetic field sensor communicating with the electromagnetic field generator when locating the operation site; and targeting the operation site using the position of the electromagnetic field sensor.

12. The method of claim 11, wherein the operation site is an acetabular operation site and positioning the blade portion of the surgical implement comprises positioning the blade portion between an acetabulum and a femoral head.

13. The method of claim 12, wherein the acetabular operation site is a portion of the acetabulum, a portion of acetabular cartilage, or a portion of labral cartilage.

14. The method of claim 12, wherein positioning the surgical implement between the acetabulum and the femoral head comprises positioning the electromagnetic field sensor of the surgical implement between the acetabulum and the femoral head.

15. The method of claim 12, wherein targeting the operation site comprises orienting an axis for drilling that extends through a portion of the ilium and the operation site.

16. The method of claim 11, wherein positioning the surgical implement comprises positioning a landmark of the surgical implement at a known position relative to the operation site, the position of the landmark being known relative to the position of the electromagnetic field sensor, and wherein targeting the operation site comprises targeting the operation site using the position of the electromagnetic field sensor and the position of the landmark.

17. The method of claim 11, wherein targeting the operation site comprises:

identifying a plurality of paths to the operation site, each path extending linearly between the operation site and a different point on the surface of a tissue surrounding the operation site; and selecting, from the plurality of paths, a particular path to use as an axis for drilling that minimizes disturbance of tissue surrounding the operation site.

* * * * *